US00PP11054P

United States Patent [19]

Brown

[11] Patent Number: Plant 11,054

[45] Date of Patent: Sep. 7, 1999

[54] AGLAONEMA PLANT NAMED 'WHITE RAIN'

[75] Inventor: B. Frank Brown, Valkaria, Fla.

[73] Assignee: Sunshine Foliage World, Zolfo Springs, Fla.

[21] Appl. No.: 09/004,127

[22] Filed: Jan. 7, 1998

[51] Int. Cl.[6] ..... A01H 5/00

[52] U.S. Cl. ..... Plt./376

[58] Field of Search ..... Plt./376

*Primary Examiner*—Howard J. Locker
*Assistant Examiner*—Melissa L. Kimball
*Attorney, Agent, or Firm*—C. A. Whealy

[57] ABSTRACT

A new and distinct cultivar of Aglaonema named 'White Rain' particularly characterized by its mostly upright and outwardly arching plant habit; very dense and full appearance; propensity to readily produce divisions; oblong and narrow leaves that are silver green in the center surrounded with medium and dark green spots and flares/streaks towards the margins; white midveins; white petioles; low temperature tolerance; and resistance to diseases common to Aglaonema.

1 Drawing Sheet

The present invention relates to a new and distinct cultivar of Aglaonema plant, botanically known as Aglaonema hybrid, and hereinafter referred to by the cultivar name White Rain.

The new Aglaonema is a product of a planned breeding program conducted by the inventor in Valkaria, Fla. The objective of the breeding program was to develop new Aglaonemas with unique and interesting leaf patterns. The new Aglaonema originated from a cross made by the inventor in 1989 of the Aglaonema hybrid cultivar Ernesto's Favorite (not patented) as the female, or seed, parent with the Aglaonema hybrid cultivar Panayensis (not patented) as the male, or pollen, parent. The cultivar White Rain was discovered and selected by the inventor as a seedling within the progeny of the stated cross in a controlled environment in Valkaria, Fla.

Plants of the female parent cultivar, Ernesto's Favorite, differ from plants of the new Aglaonema in leaf color, leaf pattern, midvein color and petiole color. In addition, plants of the new Aglaonema are fuller and denser than plants of the cultivar Ernesto's Favorite.

Plants of the male parent cultivar, Panayensis, differ from plants of the new Aglaonema in leaf color, leaf pattern and petiole color. In addition, plants of the new Aglaonema are more vigorous, more cold-tolerant and produce more divisions than plants of the male parent.

Asexual propagation of the new cultivar by divisions at Zolfo Springs, Fla., since 1989, has shown that the unique features of this new Aglaonema plant are stable and reproduced true to type in successive generations.

The new Aglaonema has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'White Rain'. These characteristics in combination distinguish 'White Rain' as a new and distinct cultivar:

1. Plants of the new Aglaonema are mostly upright and outwardly arching in plant habit.
2. Numerous leaves that are closely-spaced give plants a very dense and full appearance.
3. Plants of the new Aglaonema readily produce divisions.
4. The upper surfaces of mature leaves of plants of the new Aglaonema are silver green in the center surrounded with medium and dark green spots and flares/streaks towards the margins with white midveins.

5. The leaves of the new Aglaonema are oblong and narrow.
6. Mature leaves of plants of the new Aglaonema have white petioles.
7. Plants of the new Aglaonema are tolerant of low temperatures, that is, ambient temperatures of about 7° C. do not cause foliar damage.
8. Plants of the new Aglaonema are resistant to diseases common to Aglaonema.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective review of a typical plant of 'White Rain' in a 25.5-cm container.

The photograph at the bottom of the sheet comprises a close-up view of the upper surface of a mature leaf. Leaf colors in the photographs may appear different from the actual colors due to light reflectance.

DETAILED BOTANICAL DESCRIPTION

The following observations, measurements and comparisons describe plants grown in Zolfo Springs, Fla., under a polypropylene-covered shadehouse and conditions which closely approximate those used in horticultural practice. Plants were grown under day temperatures ranging from 21 to 38° C. and night temperatures ranging from 7 to 21° C. The polypropylene shade provided a 84 percent decrease in ambient light level. In the following description, color references are made to The Royal Horticultural Society Colour Chart except where general terms of ordinary dictionary significance are used.

Botanical classification: Aglaonema hybrid cultivar White Rain.

Parentage:

*Female, or seed, parent.*—Aglaonema hybrid cultivar Ernesto's Favorite, not patented.

*Male, or pollen, parent.*—Aglaonema hybrid cultivar Panayensis, not patented.

Propagation:

*Type.*—By division and by cuttings.

*Time to initiate roots.*—About 23 and 39 days at 32 and 21° C., respectively.

*Time to develop roots.*—About 30 and 51 days at 32 and 21° C., respectively.

*Rooting habit.*—Numerous fleshy white roots.

Plant description:

*Plant shape.*—Mostly upright and outwardly arching. Numerous leaves that are closely-spaced give plants a very full and dense appearance.

*Growth habit.*—Erect when young, becoming outwardly arching. Appropriate for 25.5-cm and smaller containers. Plants readily produce divisions.

*Plant size.*—Height, soil surface to top of leaf canopy: About 50 cm. Width: About 80 cm.

*Plant vigor.*—moderate.

*Stem description.*—Diameter at soil surface: About 2.4 cm. Internode length: About 1.75 cm. Color, mature: Green, 146A, with yellow green spots.

*Foliage description.*—Shape: Oblong, narrow. Length, fully expanded: About 29.5 cm. Width, fully expanded: About 9.5 cm. Margin: Entire. Apex: Acuminate. Base: Cuneate. Aspect: Mostly flat, slightly cupped at base. Texture: Leathery, smooth, glabrous, shiny on both surfaces. Color: Young, upper surface: Center: Green, close to 138B. White spots: 155A/154D. Midvein: White to light green, 155A/150D/154D. Green spots and flares/streaks towards margin: Medium green, close to 146B; dark green, greener than 147A. Young, lower surface: Background: Greener than 144A. White midvein, spots/streaks: 150D/154D. Mature, upper surface: Center: Silver green, close to 191A. Midvein: White, 155A. Light green/yellow spots/streaks: 151D and 154B/154C/154D. Green spots and flares/streaks towards margin: Medium green, 189A; dark green, darker than 147A. Mature, lower surface: Background: Greener than 146A. White spots/streaks: 155A. Petiole length, primary shoot: About 20 cm. Petiole diameter at apex: About 7 mm. Petiole diameter at base: About 1.75 cm. Petiole wing: Apparent on lower 70 to 80% of mature leaf petiole, about 15.5 cm in length and about 7 mm in width. Petiole color: Young: White, 155A with very light green. Mature: White, 155A.

*Inflorescence.*—Typical of Aglaonema, no commercial significance.

Disease tolerance: Plants of the new Aglaonema are resistant to diseases common to Aglaonema.

Low temperature tolerance: Plants of the new Aglaonema are tolerant of low temperatures, that is, ambient temperatures of about 7° C. do not cause foliar damage.

It is claimed:

1. A new and distinct cultivar of Aglaonema plant named 'White Rain', as illustrated and described.

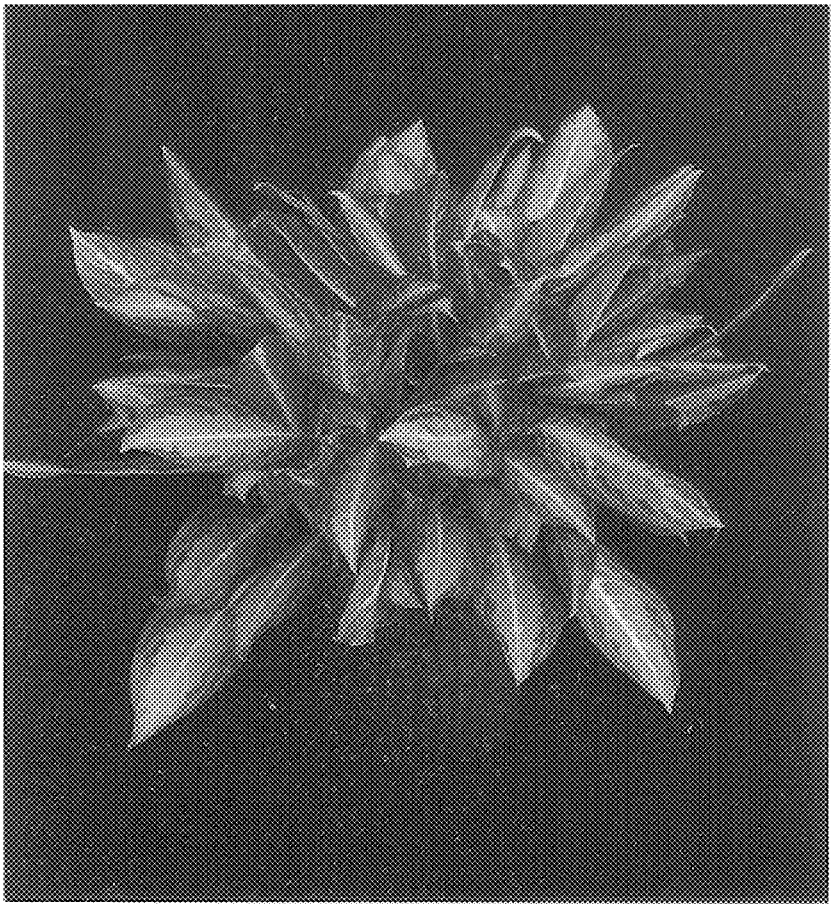
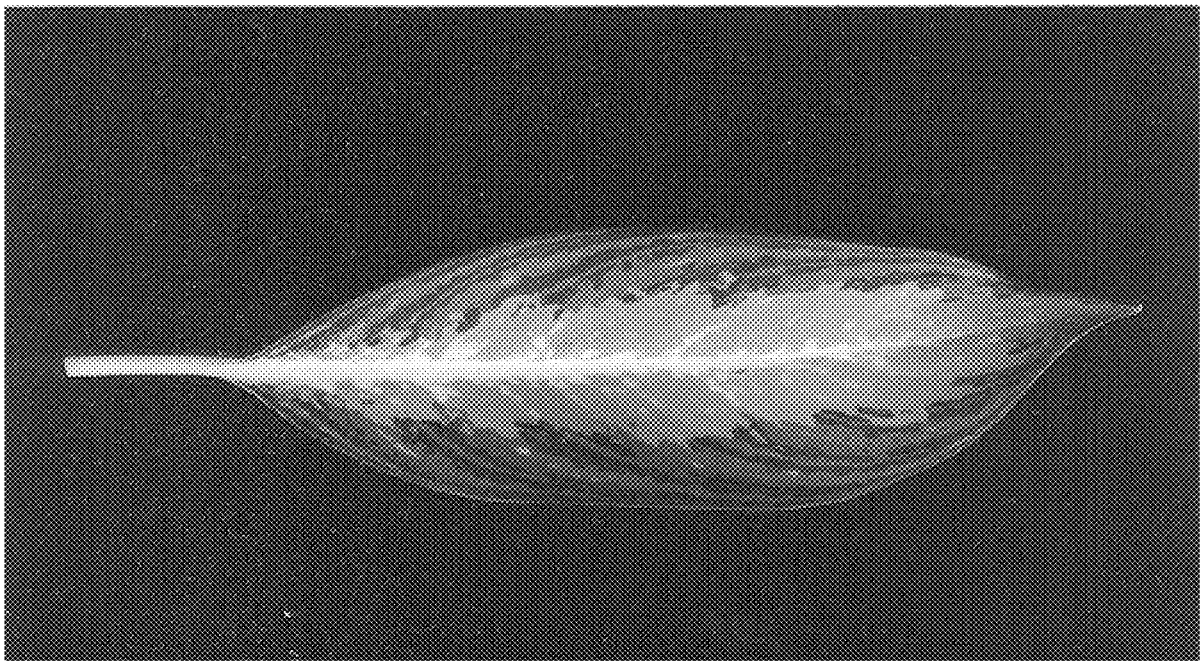

* * * * *